United States Patent
Harding et al.

(10) Patent No.: US 7,384,798 B2
(45) Date of Patent: Jun. 10, 2008

(54) METHOD OF DETECTING ANALYTES IN A MICROFLUIDIC SAMPLE AND A SYSTEM FOR PERFORMING THE SAME

(75) Inventors: Philip H. Harding, Corvallis, OR (US); Christopher C. Beatty, Albany, OR (US); Kenneth J. Ward, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/590,263

(22) Filed: Oct. 31, 2006

(65) Prior Publication Data

US 2008/0102537 A1    May 1, 2008

(51) Int. Cl.
*G01N 33/553*    (2006.01)
(52) U.S. Cl. .................................... 436/526
(58) Field of Classification Search ............. 435/4, 435/7.92, 7.1; 436/526, 514, 518, 523; 422/50, 422/55
See application file for complete search history.

(56) References Cited

U.S. PATENT DOCUMENTS

| | | |
|---|---|---|
| 4,990,075 A | 2/1991 | Wogoman |
| 5,316,726 A | 5/1994 | Babson et al. |
| 5,320,808 A | 6/1994 | Holen et al. |
| 5,827,478 A | 10/1998 | Carey et al. |
| 5,989,824 A | 11/1999 | Birmingham et al. |
| 6,136,611 A | 10/2000 | Saaski et al. |
| 6,197,494 B1 | 3/2001 | Oberhardt |
| 6,294,342 B1 | 9/2001 | Rohr et al. |
| 6,555,062 B1 | 4/2003 | Lewis et al. |
| 6,582,662 B1 | 6/2003 | Kellogg et al. |
| 6,632,399 B1 | 10/2003 | Kellogg et al. |
| 6,730,520 B2 | 5/2004 | Coassin et al. |
| 6,808,714 B2 * | 10/2004 | Dame et al. ............. 424/269.1 |
| 6,953,550 B2 | 10/2005 | Sheppard, Jr. et al. |
| 7,157,049 B2 * | 1/2007 | Valencia et al. ........... 422/68.1 |
| 2002/0076354 A1 * | 6/2002 | Cohen ......................... 422/72 |
| 2003/0095897 A1 * | 5/2003 | Grate et al. ................. 422/186 |
| 2003/0098302 A1 | 5/2003 | Yguerabide et al. |
| 2006/0129327 A1 | 6/2006 | Kim et al. |

* cited by examiner

*Primary Examiner*—Ann Y. Lam

(57) ABSTRACT

A method of detecting analytes in a microfluidic sample includes introducing at least one type of analyte, at least one type of carrier particle, and a fluid into a mixing chamber of a system. The at least one type of analyte binds to a site on the at least one type of carrier particle to form a microfluidic suspension including at least one analyte-bound particle suspended in the fluid. The at least one analyte-bound particle is separated from the fluid by exposing the suspension to physical forces, magnetic forces, or combinations thereof. A spectrophotometric property of a solution is altered using the at least one analyte-bound particle. The altered spectrophotometric property is measured with an optical detection system.

9 Claims, 3 Drawing Sheets

METHOD OF DETECTING ANALYTES IN A MICROFLUIDIC SAMPLE AND A SYSTEM FOR PERFORMING THE SAME

BACKGROUND

The present disclosure is generally directed to a method of detecting analytes in a microfluidic sample, and a system for performing the same.

Assays are often used in the biochemical, medical and environmental fields to detect the presence and/or concentration of one or more analytes. Numerous assays (including immunoassays) are known where the analyte is either an antigen or an antibody. Enzyme-linked immunosorbent assays (also known as ELISAs) have recently become popular, especially in the medical field. This may be due, at least in part, to the fact that an ELISA is capable of quantitatively determining the concentration of, for example, drug(s) in a urine sample, or detecting the presence of, for example, HIV in a blood sample. Particle-based ELISAs have recently been developed, in which antibodies are directly bound to particle surfaces. Such assays generally include the following advantages: 1) an increased surface area relative to binding antibodies to a wellplate surface, and 2) the ability to separate the particles from a liquid phase after reaction using, for example, magnetism or density difference.

Particle-based ELISAs are typically performed by first manually pipetting and mixing the various reagents, including antibodies, antigens, enzymes, other chemicals, and/or carrier particles. Particles are subsequently separated from fluids via the application of some force, for example, magnetism in conjunction with ferrous oxide particles, followed by washing. Spectrophotometric detection is typically performed by transferring (e.g., via a pipette) an aliquot of the particles to a wellplate, and then measuring the wellplate with a bench-scale optical reader. Tests are run independently, or using a simultaneous series, and the results are generally processed manually. Automated ELISA systems have recently been implemented as benchtop models to reduce time and labor costs often associated with manual ELISA systems. These automated systems may, however, require additional bulky and relatively heavy equipment, and/or typically utilize conventional wellplate approaches. Portable, automated systems using smaller, disposable coupons may be a desirable alternative to the benchtop models, however, such systems may be limited in the type of force used for particle separation.

BRIEF DESCRIPTION OF THE DRAWINGS

Features and advantages of embodiments of the present disclosure will become apparent by reference to the following detailed description and drawings, in which like reference numerals correspond to similar, though not necessarily identical components. For the sake of brevity, reference numerals or features having a previously described function may not necessarily be described in connection with other drawings in which they appear.

DETAILED DESCRIPTION

Embodiments of the method and system disclosed herein may be used to detect (i.e., determine the presence and/or quantity of) analyte(s) in a microfluidic sample. The method and system disclosed herein advantageously combine microfluidics with particle separation. Furthermore, embodiment(s) of the method advantageously incorporate an automated assay system (e.g., an immunoassay system), thereby requiring minimal operator intervention. It is believed that such a system reduces testing time and labor costs generally associated with manually performed ELISAs and manually operated wellplate readers. Furthermore, the assay system may be miniaturized (i.e., made portable), which advantageously permits a user to transport the assay system to various locations. Embodiment(s) of the miniaturized assay system advantageously use a smaller amount of materials than traditional benchtop systems, which may reduce cost and increase utility. The assay system also employs physical forces and/or magnetic forces as mechanisms for separating bound particles from the fluid suspension.

Figure 4:
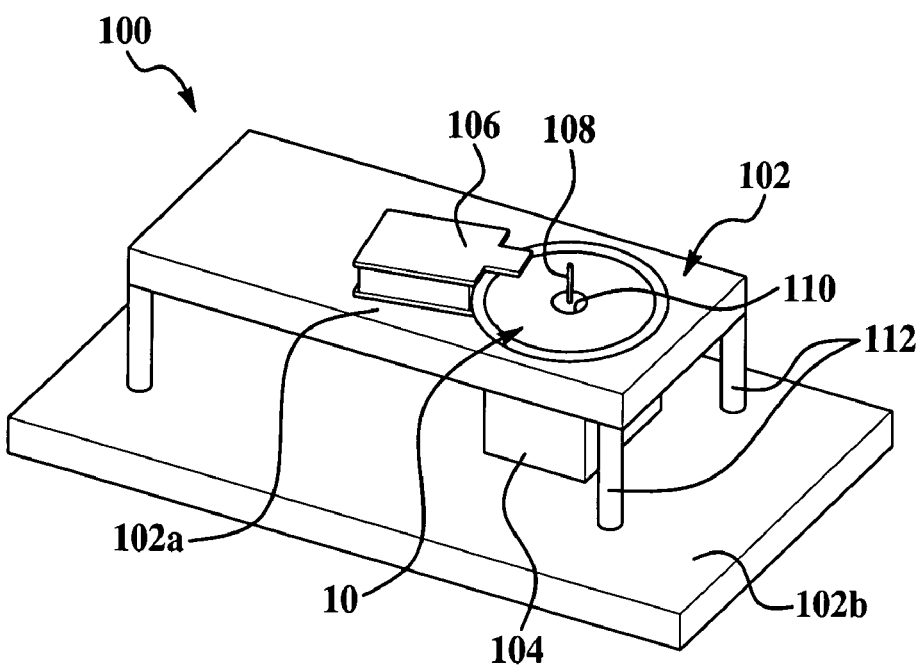
FIG. 4 is a schematic perspective view of an embodiment of an assay system.
Figure 5:
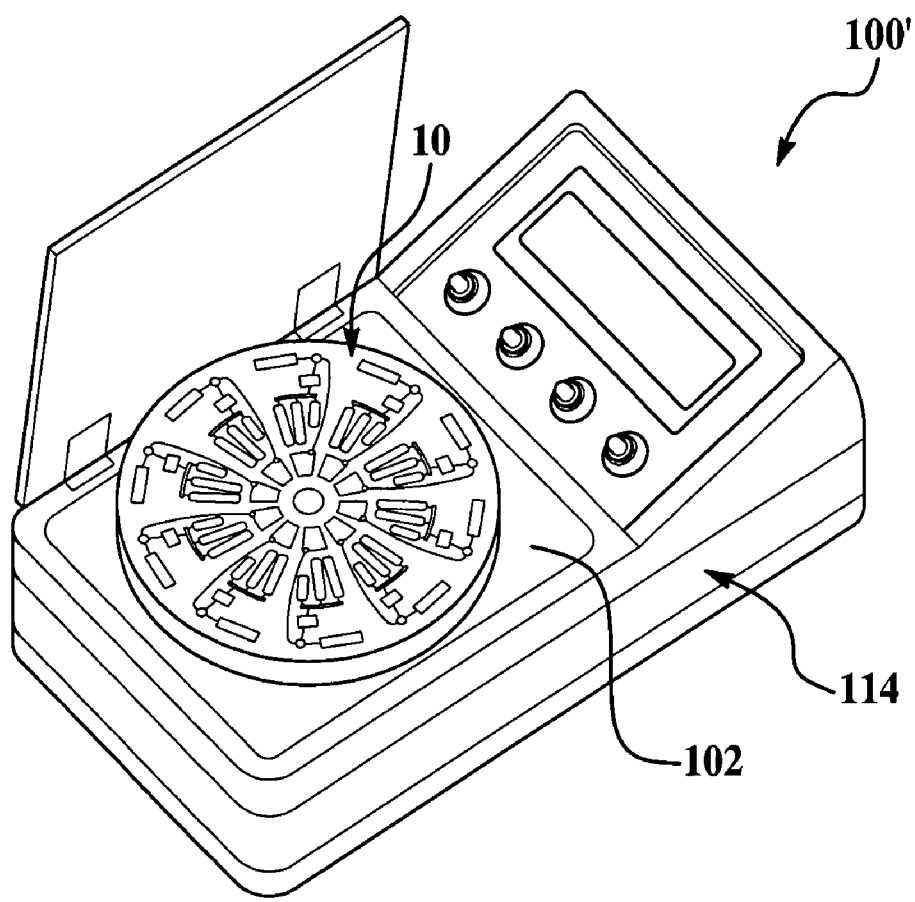
FIG. 5 is a schematic perspective view of another embodiment of an assay system.

In an embodiment, the term "portable" means that no dimension of the system 100, 100' (as shown in FIGS. 4 and 5) exceeds 9 inches.

It is to be understood that any suitable type of assay may be performed using embodiments of the method and system disclosed herein. An assay is an analysis to determine the presence, absence, or quantity of one or more components in a sample. Assays may be performed to determine the presence, absence or quantity of, for example, DNA, RNA, cytotoxicity, viruses, cellular secretions, proteins, drugs, contaminants, etc. Any assay may be performed using embodiments of the coupon and system disclosed herein, including, but not limited to antigen capture assays, bioassays, protein binding assays, four-point assays, immunoassays, microbiological assays, and many others. Very generally, assays include adding reagents, reacting the solution/suspension/mixture, and reading the generated optical signal.

Non-competitive assays (i.e., nothing added to compete with the analyte for binding), or competitive assays (i.e., conjugate added to compete with the analyte for binding) are two other non-limiting examples of suitable assays that may be performed using embodiments of the method and system disclosed herein.

A non-limiting example of a non-competitive assay includes a chemical reaction in which analytes (e.g., antigens/antibodies) bind to carrier particles (e.g., antibody- or antigen-functionalized particles). The analyte-bound carrier particles may be reacted with one or more solutions to alter a spectrophotometric property of the solution (e.g., a chromophore may be generated or changed). The altered spectrophotometric property may be optically analyzed. The resulting spectral measurements may be used to measure the presence and/or the concentration of the analyte.

A non-limiting example of a competitive assay is a competitive enzyme-linked immunosorbent assay (ELISA). The competitive ELISA involves a chemical reaction where analytes (e.g., antigens/antibodies) in a sample and their conjugates (i.e., analytes conjugated with enzymes) compete for binding sites on carrier particles (e.g., a surface functionalized with a suitable antibody/antigen or a set of antibodies/antigens). Each particle, having its multiple binding sites occupied by analytes and/or conjugates after the competition, is then separated from any fluid containing air bubbles, and unbound analytes and/or conjugates. The separated bound particles are exposed to one or more solutions to alter a spectrophotometric property of the one or more solutions. The altered property is then optically analyzed.

In one type of competitive system, chromophores in solution react with the conjugates, and thus exhibit altered spectral properties. The reaction may generate, change, or consume chromophores, thereby resulting in an increase or decrease in absorbance. The change in absorbance is then subsequently correlated with the amount or presence of analyte using any of a variety of well-known statistical methods for analyte calibration. Competitive assays are based on competing populations, and the result is generally an equilibrium between the fluid phase population (analytes and conjugates in the fluid suspension) and the surface population (analytes and conjugates bound on carrier particles). Generally, a larger analyte population in the sample results in a smaller amount of conjugates binding to the particles, thereby decreasing the optical signal generated by the conjugate.

Figure 1:
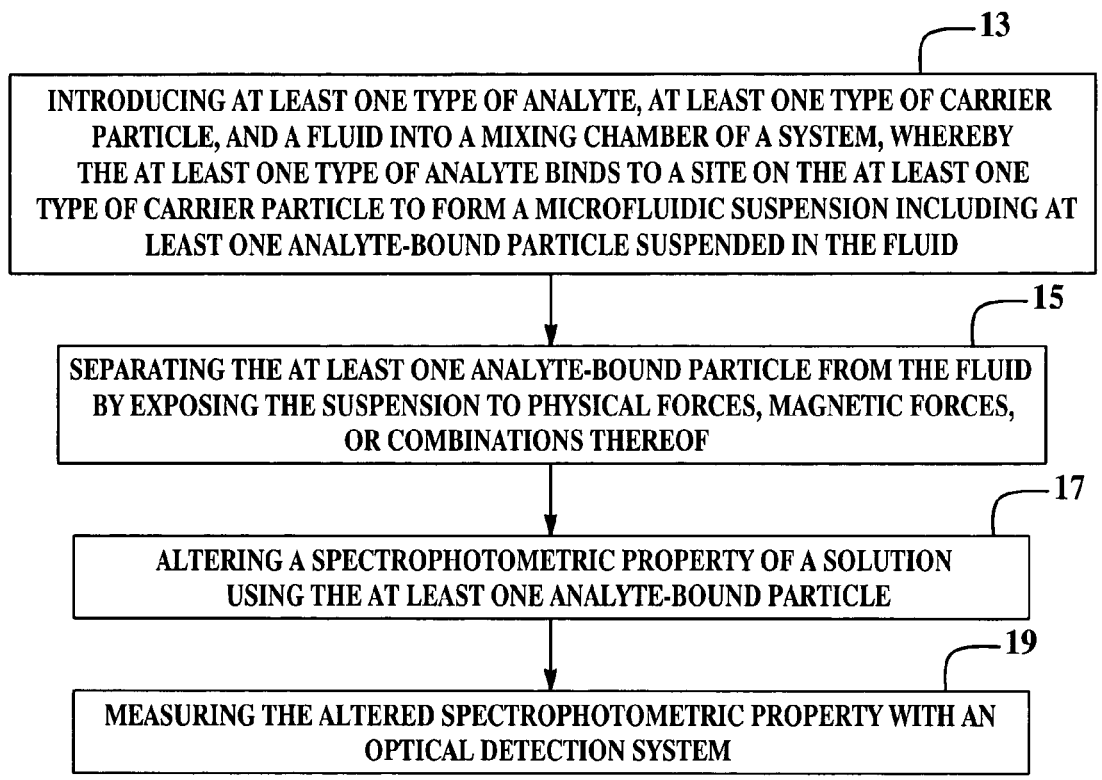
FIG. 1 is a flow diagram depicting an embodiment of the method disclosed herein.

An embodiment of the method is disclosed in FIG. 1. As depicted at reference numeral 13, the method generally includes introducing at least one type of analyte (e.g., analytes of interest contained in a liquid sample), at least one type of carrier particle (e.g., present in a colloid or suspension), and a fluid (e.g., a carrier fluid) into a mixing chamber of a system, whereby the analyte(s) binds to the carrier particle(s) to form a microfluidic suspension including at least one analyte-bound particle suspended in the fluid. The analyte-bound particle(s) is/are separated from the fluid by exposing the suspension to physical and/or magnetic forces, as shown at reference numeral 15. A spectrophotometric property of a solution is altered using the at least one analyte-bound particle, as shown at reference numeral 17; and the altered spectrophotometric property is measured with an optical detection system, as shown at reference numeral 19.

Another, more specific, embodiment of the method disclosed herein includes performing a competitive ELISA wherein an analyte and an enzyme-conjugate compete for the numerous antibody sites on each carrier particle (the general concept of which is explained hereinabove). This embodiment of the method is disclosed further hereinbelow in reference to FIG. 3. Very generally, however, an embodiment of this method includes filling reservoirs (shown in FIG. 3) with desirable components (e.g., samples, colloids, suspensions, etc.), and delivering the components to a mixing tank. Incubation enables a reaction between at least some of the components. The reaction mixture (e.g., a suspension) is delivered to a detection chamber where separation of bound particles takes place via exposure to physical and/or magnetic forces. A potential chromophore solution is delivered to the detection chamber, thereby forcing liquid containing air bubbles, and unbound analyte and conjugate out of the detection chamber. The potential chromophore solution and bound particles remain in the detection chamber where they react. This reaction results in the formation or alteration of liquid phase optical properties (e.g., absorbance, fluorescence or chemiluminescence), which are optically detected.

Figure 2:
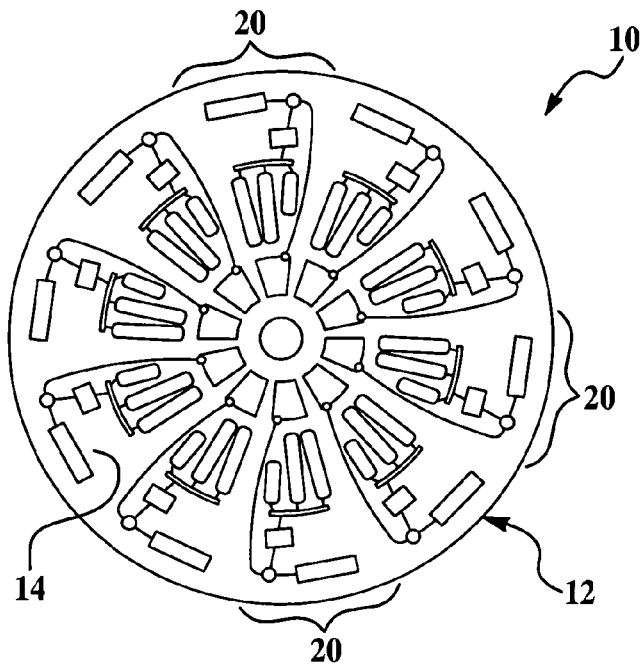
FIG. 2 is a semi-schematic top view of an embodiment of a rotatable coupon for an assay system.

With reference now to FIG. 2, an embodiment of a rotatable coupon 10 of the assay system (shown as 100 in FIG. 4 and 100' in FIG. 5) is depicted. In an embodiment, the rotatable coupon 10 is a micro-fluidic coupon and is useful for micro-scale (i.e., sample and reagent volumes less than about 100 microliters; or ranging from about 100 microliters to about 200 microliters) assay systems.

As shown in FIG. 2, the coupon 10 has a substantially circular configuration and includes a plurality of individual, or discrete, tracks 20 arranged about the circular configuration. Each individual track 20 includes various components (described further hereinbelow) that are formed integrally with a coupon body 12 or are individually secured to a base 14 of the coupon 10. In an embodiment, each track 20 is formed via conventional injection molding. It is to be understood that other suitable techniques may be used to form the coupon 10. It is to be further understood that the coupon 10 and its various components may be fabricated from a material or a variety of materials that are suitable for particular applications. Selection of the material(s) for the coupon 10 may depend, at least in part, on structural requirements, manufacturing processes and/or chemical compatibility with reagents and/or samples. Non-limiting examples of suitable materials for the coupon 10 (and its track 20 components) include inorganic crystalline or amorphous materials, such as silicon, silica, quartz, and/or glass, or organic materials, such as polymeric materials (e.g., polycarbonate, polystyrene, polypropylene, polymethylmethacrylate, etc.), and/or combinations thereof. The coupon 10 may also be made of a composite or combination of the previously mentioned materials.

In an embodiment, ten individual tracks 20 are provided to complete the coupon 10. It is to be understood that any number of tracks 20 may be used to form the coupon 10. During use, the assay performed in one track 20 may be the same or different from an assay performed in any of the other tracks 20. Further, the assay performed in a subset of tracks 20 (e.g., four tracks 20), may be the same or different from an assay performed in another subset of tracks 20. It is believed that the replication of assays on multiple tracks 20 may be useful for both calibration and for improving measurement precision.

It is to be understood that the coupon 10 may be large enough to be incorporated into a benchtop system, or may be small enough to be incorporated into a portable system. In some embodiments, the small portable coupon may be incorporated into a benchtop system. In an embodiment, the coupon 10 is a microfluidic coupon having individual tracks 20 that are capable of handling volumes of fluid on the order of microliters (e.g., less than about 100 microliters; or ranging from about 100 microliters to about 200 microliters). This type of coupon 10 may have a diameter up to about 6 inches, and a height up to about 5000 micrometers. In an embodiment, the diameter of coupon 10 is about 8 cm, and the height/thickness of coupon 10 ranges from about 5 mm to about 10 mm. Further, the size of the track 20 may vary, depending, at least in part, on the desirable size for the coupon 10 and the number of tracks 20 included.

Figure 3:
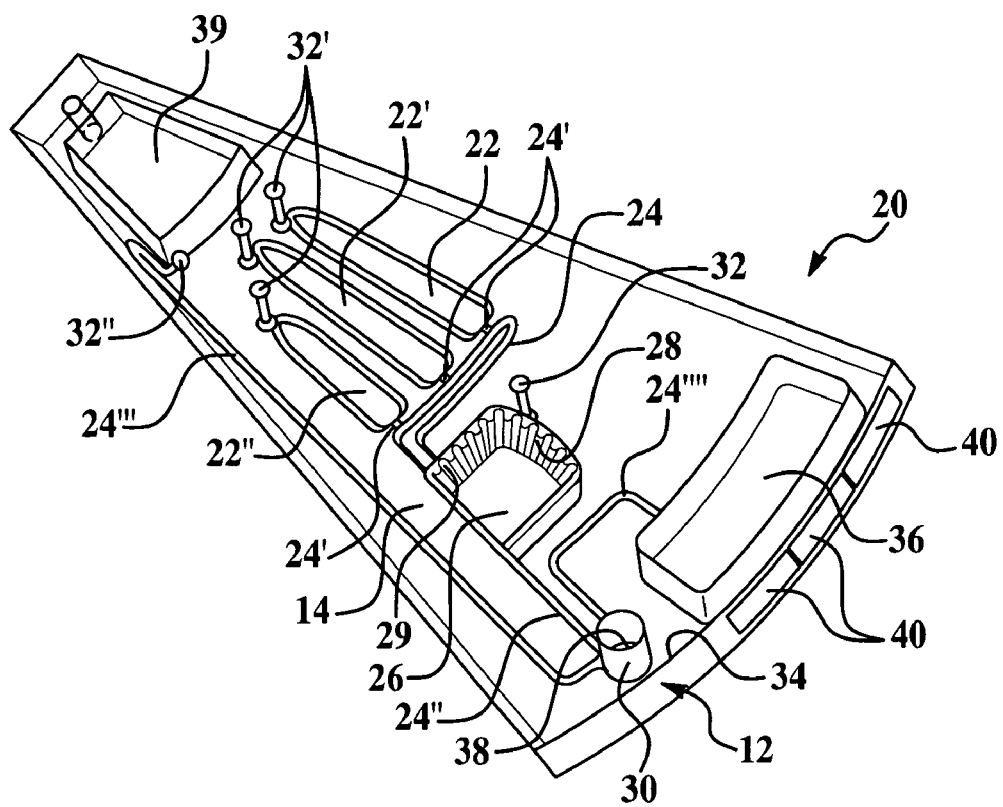
FIG. 3 is a semi-schematic top perspective view of an embodiment of a single track of an embodiment of the rotatable coupon.

With reference now to FIG. 3, an embodiment of an individual track 20 of the coupon 10 shown in FIG. 2 is depicted. The track 20 includes at least one holding reservoir 22, 22', 22" (three of which reservoirs are shown in FIG. 3). Any desirable number of holding reservoirs 22, 22', 22" may be included, and the total number may depend, at least in part, on the materials and chemistry desired for a particular assay. In the non-limiting example shown in FIG. 3, one reservoir 22" is configured to hold a test sample, another reservoir 22' is configured to hold a colloid or suspension of carrier particles, and the other reservoir 22 is configured to hold a liquid containing the enzyme-conjugate.

The test sample generally is a liquid sample containing an analyte of interest. Non-limiting examples of analytes of interest include chemical and biochemical atoms, molecules, complexes, etc. (e.g., minerals, herbicides, contaminants, DNA, RNA, proteins, drugs, viruses, bacteria, hormones, etc.).

As defined herein, a "carrier particle" is any suitable particle having a functionalized surface that is chemically attracted to, and capable of binding to the analyte and/or conjugates thereof. The functionalized surface may be formed by binding a molecule (e.g., an antibody to the analyte) to the particle surface. The carrier particles are generally small enough (i.e., ranging from 10 nanometers to about 1 micrometer) to enable their suspension in a liquid.

The particle portion of the carrier particle may be selected to have a density sufficient to separate upon introduction of physical forces and/or a property (e.g., paramagnetic or ferromagnetic) sufficient to respond to magnetic forces. Suitable carrier particles include those that are responsive to a magnetic field, and/or those that may be readily separated from its liquid suspension by physical forces. In an embodiment, each particle has both the sufficient density and the sufficient magnetic property. In another embodiment, at least some of the particles have the sufficient density and at least some other of the particles have the sufficient magnetic property. It is to be understood that any other combination of carrier particles may be used in the embodiments disclosed herein. A non-limiting example of suitable carrier particles includes micro-scale ferrous oxide particles.

In an embodiment (particularly for a competitive assay), a liquid containing enzyme-conjugate is provided in, for example, the third reservoir 22. As defined herein, a "conjugate" is an analyte having an enzyme bound thereto. As previously described, conjugates are used in competitive assays and compete with analytes for binding sites on the carrier particles.

Each of the holding reservoirs 22, 22', 22" in an embodiment may have any desirable dimensions (length, width, height). Generally, the dimensions may be the same or different for each of the reservoirs 22, 22', 22", and may depend, at least in part, on the amount and properties of the substance to be contained within the reservoirs 22, 22', 22". As a non-limiting example, FIG. 3 depicts that the holding reservoir 22" (e.g., configured to hold the test sample) is smaller than the other two holding reservoirs 22, 22'. Generally, the reservoir 22, 22', 22" volumes are a function of conjugate concentration, carrier particle suspension concentration, and sample volume. As such, the size of the respective reservoirs 22, 22', 22" may vary, depending, at least in part, on the type of substance and/or the amount of substance to be contained therein.

The holding reservoirs 22, 22', 22' are fluidly connected to (or in fluid communication with) a single mixing chamber 26 by at least one micro-channel or capillary 24. Fluid connection between respective components is achieved by providing a plurality of micro-channels 24 throughout each track 20. It is to be understood that fluid connection or communication may be selective, as micro-valves 32, 32', 32" (described further hereinbelow) or other sealing members (not shown) may be provided between the component(s) and the micro-channels 24, and opened when desired.

It is to be understood that the terms fluid(ly) "connect/connected/connection" or "communicate/communication" and/or the like are broadly defined herein to encompass a variety of divergent connected arrangements and assembly techniques. These arrangements and techniques include, but are not limited to (1) the direct fluid communication between one component and another component with no intervening components therebetween; and (2) the fluid communication of one component and another component with one or more components therebetween, provided that the one component being "fluidly connected to" the other component is somehow in operative fluid communication with the other component (notwithstanding the presence of one or more additional components therebetween). Additionally, two components may be permanently, semi-permanently, or releasably engaged with and/or coupled to one another.

As shown in FIG. 3, the micro-channel 24 is connected to a plurality of smaller micro-channels 24'. Each of the plurality of smaller micro-channels 24' respectively fluidly connects one of the holding reservoirs 22, 22', 22" to the micro-channel 24. In an embodiment, the size of the micro-channels 24, 24' is up to about 1 millimeter.

In an embodiment of the method, fluid (suspension, solutions, mixtures, etc.) flows out of each of the holding reservoirs 22, 22', 22" through the respective micro-channels 24' into the micro-channel 24 and ultimately into the mixing chamber 26. The flow of fluid from the respective chambers 22, 22', 22" may be initiated by physical forces generated by rotating the coupon 10 at a speed ranging from about 300 rpm to about 10,000 rpm. Generally, the desired speed of rotation depends, at least in part, on the type of fluid flowing through the micro-channel(s) 24, 24', and the desirable amount of fluid flow. For example, a fluid with a higher density or a higher viscosity will flow less rapidly than those fluids having lower densities or lower viscosities, given the same geometric and rotational parameters.

In an embodiment, emptying (or partially emptying) the holding reservoirs 22, 22', 22" into their respective micro-channels 24' occurs simultaneously, and is initiated upon simultaneously opening micro-valves 32' and rotating the coupon 10. The rate of fluid flow through the micro-channels 24, 24' may be controlled by the rotation speed of the coupon 10 as well as opening and closing of the micro-valves 32'.

In this embodiment, when the test sample, the carrier particle suspension, and the conjugates converge into the micro-channel 24, the three assay components start mixing before they enter the mixing chamber 26. Once inside the mixing chamber 26, the components become mixed more thoroughly to form the fluidic suspension. It is to be understood that the suspension may remain in the mixing chamber 26 or may be transferred (via rotation of the coupon 10 at suitable speeds) to a detection chamber 30 (described further hereinbelow) for optical analysis. In either embodiment, the suspension is allowed to incubate for a predetermined incubation period, which depends, at least in part on the analyte of interest and the other components used in the assay. It is to be understood that the incubation conditions (e.g., temperature, pressure, etc.) may vary depending on the assay being performed.

In another embodiment, the contents of the respective reservoirs 22, 22', 22' may be emptied or partially emptied into the mixing chamber 26 sequentially. For example, the test sample may be added, and then the conjugate, and then the carrier particles suspension. In still another embodiment, two reservoirs' (e.g., 22, 22') contents may be added simultaneously, and then the contents of the third reservoir 22" may be added (e.g., an analyte conjugate if performing a competitive ELISA). As a non-limiting example of the latter embodiment, the test sample (containing the analyte) and the carrier particles may be transferred to the mixing chamber 26 substantially simultaneously, and then the conjugate may be added. This is often referred to as a "sandwich" ELISA. It is to be understood that other desirable flow sequences (e.g., for other types of ELISAs) are contemplated as being within the purview of the present disclosure.

For merely illustrative purposes, the following description of the assaying process will be described as a competitive assay.

The addition of the analyte-containing liquid sample, carrier particle suspensions, and conjugate solutions into the mixing chamber 26 results in the formation of a fluidic suspension. As previously described, the incubating and separating processes may be accomplished in the mixing chamber 26 or in the detection chamber 30. In general, a competitive assay is initiated when the antibody-bound carrier particles come into contact with analytes and conjugates in the fluid. As previously described, each particle has a population of antibodies bound to the surface, resulting in numerous conjugate binding sites per particle (i.e., functionalized surfaces). The analytes and the conjugates compete for these binding sites with a subsequent distribution between analyte and conjugate populated sites. The bound particles are suspended in the fluid. It is to be understood that the microfluidic suspension may also include air bubbles, lone (unbound) analytes or conjugates, non-reacted materials and, possibly, some by-products or impurities.

In an embodiment, the analyte/conjugate-bound particles may be separated from the fluidic suspension inside the mixing chamber 26 or inside the detection chamber 30. When incubation occurs in the mixing chamber 26, separation may occur in the mixing chamber 26, or the fluidic suspension may be transferred to the detection chamber 30 for separation. When incubation occurs in the detection chamber 30, separation also occurs in the detection chamber 30. In still another embodiment, an intermediate chamber (not shown) may be fluidly connected between the mixing chamber 26 and the detection chamber 30 to act as an incubation/separation chamber. When an intermediate chamber is used, an embodiment of the method includes mixing the components in the mixing chamber 26, incubating and separating in the intermediate chamber, and detecting in the detection chamber 30.

It is to be understood that the mixing chamber 26, the detection chamber 30, the channels 24, 24', 24", 24'", 24"" (described further hereinbelow), and/or combinations thereof may include physical features 29 defined in or on respective surfaces thereof. A non-limiting example of such a feature 29 is shown defined in the surface 28 of the mixing chamber 26. Such features 29 may be configured to physically trap the bound particles. Non-limiting examples of such features 29 include grooves (shown defined in surface 28), channels, pits, bumps, or any other roughened surface, or combinations thereof.

Generally, particle separation occurs by rotating the coupon 10 at relatively high, controlled speeds. It is to be understood that speeds suitable for separation are generally higher than the speeds used for transporting fluid throughout the tracks 20 of the coupon 10. Suitable speeds for physical separation of the bound carrier particles from the fluid in the fluidic suspension range from about 1000 rpm to about 10,000 rpm. These higher rotational speeds generate a centrifugal force inside the mixing chamber 26, or the detection chamber 30 (wherever separation is taking place) to physically separate the bound particles from the fluid, and retain the bound particles against a respective outer radial surface 28, 38 of the mixing chamber 26 or the detection chamber 30. The bound particles typically have a higher density than the fluid, and thus mechanically entrain on the respective surface 28, 38 of the mixing chamber 26 or the detection chamber 30 in response to the applied centrifugal force. In an embodiment and as previously described, the surface(s) 28, 38 may also be roughened or otherwise textured (i.e., include physical feature(s) 29) to facilitate particle retention thereto.

It is to be understood that separation may also occur in the channel 24" that fluidly connects the mixing chamber 26 with the detection chamber 30.

Separation of the bound particles from the fluid suspension may be accomplished by generating a magnetic field inside the mixing chamber 28 or the detection chamber 30. Magnetic forces are used to attract the bound particles to the respective inner surface 28, 38. For magnetic separation to occur, the carrier particles selected have magnetic properties, and, thus, are magnetically attracted to the generated magnetic field.

As depicted in FIG. 3, to generate the magnetic field, at least one magnet 40 is disposed or otherwise established about the outer edge 34 of the track 20 (which may also be an outer edge of the coupon 10). It is to be understood that a plurality of magnets 40 may be provided about the periphery of a single coupon 10 when a plurality of tracks 20 is arranged to form the coupon 10.

Alternatively, the magnets 40 may be disposed in any location on the coupon 10 where particle retention may be desirable. As a non-limiting example, it may be desirable to retain the particles either under or over the coupon 10. In such an embodiment, at least one magnet 40 may be disposed above or below each track 20. This type of magnet 40 may be particularly desirable when separation occurs in the mixing chamber 26 or in the intermediate chamber (not shown). The placement of the magnet 40 prohibits the separated bound particles from leaving the mixing chamber 26 prior to a desirable time. This may also be desirable so that magnets 40 or the particles do not interfere with an optical detection system measuring through the transparent detection chamber 30.

Another non-limiting example includes positioning the magnets 40 in predetermined areas so that a directed magnetic field is generated in some areas and not in other areas of the coupon 10. Multiple magnets 40 may be used in two different positions, thereby allowing the particles to be retained twice, in different areas of the track 20. The magnets 40 may be provided as one continuous magnet, non-limiting examples of which include a ring outlining the perimeter of the coupon 10 or a slab disposed under a portion of, or under the entire bottom surface of the coupon 10. Some of the magnet 40 placements are useful for performing an assay in one track 20 at a time, in some tracks 20 and not others, and/or in all tracks 20 simultaneously.

The magnets 40 may generally be provided as permanent magnets, removable magnets, electromagnets, or the like, or combinations thereof. The magnet(s) 40 may have various shapes, and may have different strengths, depending on the application thereof.

In an embodiment, separation of the bound particles from the fluid in the fluidic suspension is accomplished by a combination of physical and magnetic forces. The method of the present disclosure advantageously uses a system that is capable of performing each separation mechanism separately, sequentially, or simultaneously. As a non-limiting example, particle separation using both physical and magnetic forces may be accomplished by providing magnetically attracted carrier particles, and driving the particles within the mixing chamber 26 or the detection chamber 30 outwardly (toward the respective surface 28, 38 or the surface of channel 24") via a generated magnetic field and by centrifugal force generated by spinning or rotating the coupon 10 at high speeds. The forces together drive the particles toward the surface 28, 38 (or the surface of the channel 24"). The simultaneously applied physical and magnetic forces separate the bound particles from the fluid in the fluidic suspension, and retain the particles inside the mixing chamber 26, the detection chamber 30, or the channel 24" that fluidly connects the chambers 26, 30. The forces may be used to keep the particles from being washed into a waste chamber 36 (which is fluidly connected to the mixing chamber 26 (not shown) and/or the detection chamber 30 (shown in FIG. 3)) with the rinse solution (a non-limitative example of which includes the chromophore solution described hereinbelow) and the fluid. During washing, the respective chambers 26, 30 may be vented to allow air out and liquid in.

It is to be understood that venting may also be used during release of the components from the respective reservoirs 22, 22', 22" during mixing, and/or during the transfer of the various liquids throughout the track 20.

In an embodiment in which separation occurs in the detection chamber 30, the fluid suspension is transferred from the mixing chamber 26 to the detection chamber 30 that is in fluid communication with the mixing chamber 26 via micro-channel 24". It is to be understood that the transfer may take place before or after incubation, depending on which chamber 26, 30 one desires incubation to take place in. A non-limitative example of the detection chamber 30 is a substantially transparent cuvette. In an embodiment, transferring the fluid suspension is accomplished by opening a micro-valve 32 and applying physical forces sufficient to move the suspension through the micro-channel or capillary 24". Physical forces again result from rotational movement of the coupon 10.

The detection chamber 30 is generally a rounded (e.g., having a cylindrical, oval or ellipse shape) or rectangularly-shaped, optical cuvette (i.e., a transparent cuvette) advantageously located at an outer edge 34 of the track 20. This positioning may be desirable to facilitate relative ease of optical detection. Non-limiting examples of suitable materials for the detection chamber 30 include glass, plastics (such as polycarbonate, polystyrene, and/or the like), or any other material that minimizes scattering and absorption of light when the detection chamber 30 is scanned by the optical reader. Plastics may be particularly desirable because they are less apt to shatter or crack under pressure caused from centrifugal force generated by rotation of the coupon 10 at relatively high speeds. In an embodiment, the detection chamber 30 has a volume ranging from about 1 microliter to about 100 microliters.

A potential chromophore solution is held in a potential chromophore reservoir 39 until reaction with the bound particles is desirable. In one embodiment, the solution may be delivered to the detection chamber 30 after separation has occurred. In other embodiments, the potential chromophore solution is delivered to the mixing chamber 26 after separation has occurred. The potential chromophore solution may also be delivered to the detection chamber 30 and/or the mixing chamber 26 before separation has occurred.

In the embodiment shown in FIG. 3, a micro-valve 32" is opened, and the potential chromophore solution flows out of the reservoir 39, through a micro-channel 24''', and into the detection chamber 30. Fluid movement is initiated by rotating the coupon 10 (as previously described). In an embodiment, the potential chromophore solution is delivered to the detection chamber 30 in excess. The excess potential chromophore solution is then delivered to the waste reservoir 36 via a micro-channel 24"" by rotating the coupon 10 (as previously described). It is to be understood that the potential chromophore solution may be used to flush the excess and unbound components from the detection chamber 30, thereby eliminating a relatively time-consuming wash step often used in ELISA assays.

In an embodiment of the method disclosed herein, the analyte concentration is determined via the alteration (i.e., modification, increase or decrease) of a spectrophotometric property of a solution that is reacted with the bound particles. In an embodiment, the spectrophotometric property is the signal exhibited by a chromophore in the solution. In one embodiment, the potential chromophore solution includes chromophores, which exhibit a corresponding spectrophotometric property. The reaction with the bound particles may alter the chromophore(s), thereby altering a spectrophotometric property of the solution. In another embodiment, the potential chromophore solution includes molecules that generate chromophore(s) after reaction with an antigen or an enzyme conjugate, and a corresponding spectrophotometric property, when reacted with the bound particles.

If separation occurs in the detection chamber 30, the applied physical and/or magnetic forces separate the bound particles from the fluid, and retain the particles inside the detection chamber 30 when the remaining fluid is washed away and into the waste chamber 36. The bound particles are exposed to the potential chromophore solution (e.g., well-known ELISA chromophores, including but not limited to tetramethylbenzidine (TMB), red or green fluorescent protein (RFP, GFP), retinal, anthranilic acid, 4-aminoantipyrine (e.g., for absorbance), N,N-Dibutylphenylenediamine (DB-PDA) (e.g., for fluorescence), or the like, or combinations thereof). In an embodiment, the potential chromophore solution(s) reacts with the enzyme conjugate, which either consumes or generates chromophores, which decreases or increases the generated signal. This optical signal is detectable via an operatively positioned optical detection system. In a non-limiting example, the conjugate on the retained bound particles reacts with the potential chromophore solution, thereby producing a colored species. This chromophore species then diffuses into the bulk liquid.

As described hereinabove, the optical signals are generated or altered when the potential chromophore solution reacts with, in the case of the competitive assay, the enzyme-conjugate on the bound particles. Detection may generally be performed via spectrophotometers. When chromophores are generated or altered in the detection chamber 30 via the reaction between the bound particles and the potential chromophore solution, kinetic optical measurements may be performed to determine the rate of chromophore generation or alteration over time. The measured signals are then analyzed to determine the original concentration of the analyte or conjugate. In a competitive assay where a higher analyte concentration results in a lower fraction of bound enzyme-conjugate and thus a lower optical signal, the concentration of analytes may be determined by comparing the spectrophotometric signal against a battery of analyte standards used for calibration, and interpolating mathematically.

In another embodiment of the method, and as previously described, the fluid suspension may remain in the mixing chamber 26 for separation of the bound particles from the fluid. After separation, the mixing chamber 26 may be flushed out so that excess sample, unbound analytes and unbound conjugates are washed from the chamber 26. In this embodiment, the mixing chamber 26 may be fluidly connected to the waste chamber 36, which receives the excess sample, unbound analytes and unbound conjugates. The bound particles are held in the chamber 26 via the physical and/or magnetic forces during the wash.

After the excess and unbound components are removed from the chamber 26, the potential chromophore solution(s) (from the chromophore reservoir 39, which in this embodiment is also fluidly connected to the mixing chamber 26) is introduced into the chamber 26. It is to be understood that the potential chromophore solution may also be used to flush the excess and unbound components from the chamber 26.

In this embodiment, the reaction between the bound particles and the potential chromophore solution(s) takes place in the mixing chamber 26. It is to be understood that the optical detection system may be positioned to perform kinetic measurements of chromophore generation/alteration within the mixing chamber 26. Alternatively, the reacted solution may then be transferred (via physical forces) at some point in time to the detection chamber 30 for optical detection. It is to be understood that since the reaction does not take place in the detection chamber 30, single measurements are made as the reacted chromophores are transferred to the detection chamber 30 (as opposed to the kinetic measurements made during chromophore generation/alteration).

Referring now to FIG. 4, an embodiment of the immunoassay system 100 is depicted. The rotatable coupon 10 is removably disposed in, or is otherwise removably established on a platform 102. The coupon 10 is disposed so that it is operatively connected to a motor 104. In an embodiment, an optical detection system 106 is disposed or otherwise established on the platform 102. It is to be understood that the optical detection system 106 may also be separate from the platform 102.

The platform 102 acts as a support system for receiving the rotatable coupon 10 therein. As shown in FIG. 4, the platform 102 is multi-leveled, where the coupon 10 and the optical detection system 106 is supported by an upper surface 102a, and the motor 104 is supported on a lower surface 102b. The upper surface 102a is supported a spaced distance from the lower surface 102b by a plurality of spacers, as denoted by support rods 112. The platform 102 is made from any suitable rigid material, such as aluminum, steel, polycarbonates, polyacrylics, or the like, or combinations thereof. Since the coupon 10 is configured for microfluidic applications, the platform 102 may be large enough to support the coupon 10, the motor 104 and the optical detection system 106. As a non-limiting example, the platform 102 has a height ranging from about 0.2 centimeters to about 1.5 centimeters, and a length of about 5 inches. The platform 102 may be larger or smaller, as desired.

In an embodiment, the motor 104 may be a stepper motor or a servomotor. The motor 104 is generally disposed adjacent to (e.g., below) the coupon 10 on the lower surface 102b of the platform 102. In one embodiment, the motor 104 operatively connects to the coupon 10 by a rotational pin 108 that captures the coupon 10 through an aperture 110. The motor 104 may be operatively connected to the coupon 10 via any other suitable means, for example, a screw configuration, or the like. The motor 104 is configured for rotating the coupon 10 on demand in either a clockwise or counter-clockwise direction. This bi-directional movement may be advantageous for the delivery of various fluids given a particular microfluidic architecture. Bi-directional movement may also be advantageous to position and reposition the coupon 10 and to align the optical detection system 106 with the detection chamber 30 (or the mixing chamber 26).

For example, the motor 104 may manipulate the positioning of the coupon 10 by rotating the coupon 10 in short intervals until the desired position of the coupon 10 is achieved. Alternatively, the coupon 10 may be rotated at relatively high speeds for long intervals of time to facilitate liquid movement and/or particle separation.

The optical detection system 106 may be any suitable device that reads signals emitted by the chromophore when it reacts with bound particles. The optical detection system 106 includes at least a light source (e.g., LED, filaments, arc, plasma, laser, etc.) and an optical detector (e.g., photodiode, CCD, thermistor, etc.). The optical detection system 106 may also include other elements, such as filters, gratings, prisms, etc. The optical detection system 106 is generally compact or suitably small enough to be supported on the upper surface 102a of the platform 102, adjacent the coupon 10. Suitable optical detection systems 106 for use in the assay system 100 may include those configured to measure absorbance (where the light source is positioned on one of the top or bottom of the coupon 10, and the optical detector is positioned on the other of the bottom or top of the coupon 10), those configured to measure fluorescence (where the light source is positioned on the top or bottom of coupon 10, and the optical detector is positioned near the outer edge (i.e. substantially parallel to the coupon diameter) of the coupon 10 for orthogonal detection), and/or those configured to measure chemiluminescence.

In an embodiment, the optical detection system 106 may be removably attached to the platform 102 to facilitate positioning and repositioning of the optical detection system 106 at any angle to properly locate and read the signals emitted from within the detection chamber 30. In another embodiment, the immunoassay system 100 does not include an optical detection system 106, but may instead be configured to operatively function with a detached optical detection system 106 to read the signals.

FIG. 5 depicts another embodiment of the immunoassay system 100'. In this embodiment, the system 100' is built into a single unit, suitably miniaturized so as to facilitate portability thereof. The platform 102, motor 104 and the optical reader 106 are operatively included within the system body 114, and may be pre-programmed to perform the necessary functions for detecting the analyte in a test sample. This portable, automated immunoassay system 100' further includes components that will enable particle separation based on physical forces (e.g., by spinning or rotating the coupon 10 by operation of the motor 104) and/or magnetic forces (e.g., by disposing at least one magnet 40 on the coupon 10 to generate a magnetic field to attract magnetically responsive particles).

As shown in FIG. 5, the coupon 10 is removable from the system 100'. It is to be understood that when the coupon 10 is inserted onto platform 102 of the system 100', it engages the motor 104, and is operatively positioned so as to enable optical detection.

The fluids (i.e., the test sample, suspension of conjugates, and suspension of carrier particles) are manually added to their respective holding reservoirs 22', 22, however, the fluid movement, fluid reaction, incubation, particle separation and detection procedures are accomplished automatically. The sample is introduced when an assay is desired, however, the reagents (e.g., conjugates, particle suspension, chromophore) may be pre-loaded during coupon 10 manufacturing.

While several embodiments have been described in detail, it will be apparent to those skilled in the art that the disclosed embodiments may be modified. Therefore, the foregoing description is to be considered exemplary rather than limiting.

What is claimed is:

1. A method of detecting analytes in a microfluidic sample, comprising:
   introducing at least one type of analyte, at least one type of carrier particle, and a fluid into a mixing chamber of a system, whereby the at least one type of analyte binds to a site on the at least one type of carrier particle to form a microfluidic suspension including at least one analyte-bound particle suspended in the fluid;
   separating, in an optical detection chamber, the at least one analyte-bound particle from the fluid by exposing the suspension to physical forces, magnetic forces, or combinations thereof;
   altering, in the optical detection chamber, a spectrophotometric property of an other solution introduced into the optical detection chamber using the at least one analyte-bound particle; and
   measuring, in the optical detection chamber, the altered spectrophotometric property with an optical detection system;
   wherein the system includes:
      a rotatable coupon; and
      a plurality of tracks defined in the rotatable coupon, each of the plurality of tracks including at least one respective fluid reservoir, a respective mixing chamber, and a respective optical detection chamber.

2. The method as defined in claim 1 wherein physical forces are generated by rotating the rotatable coupon at a speed ranging from about 1,000 rpm to about 10,000 rpm using a motor operatively connected to the rotatable coupon.

3. A method of detecting analytes in a microfluidic sample, comprising:
   introducing at least one type of analyte, at least one type of carrier particle, and a fluid into a mixing chamber of a system, whereby the at least one type of analyte binds to a site on the at least one type of carrier particle to form a microfluidic suspension including at least one analyte-bound particle suspended in the fluid;
   separating, in an optical detection chamber, the at least one analyte-bound particle from the fluid by exposing the suspension to physical forces, magnetic forces, or combinations thereof;
   altering, in the optical detection chamber, a spectrophotometric property of an other solution introduced into the optical detection chamber using the at least one analyte-bound particle; and
   measuring, in the optical detection chamber, the altered spectrophotometric property with an optical detection system;
   wherein the other solution includes potential chromophores, and wherein the method further comprises:
   washing the fluid, any unbound analyte, and any unbound carrier particles into a waste chamber; and
   introducing the other solution to the analyte-bound particle, thereby altering the spectrophotometric property of the solution.

4. The method as defined in claim 3 wherein separating the at least one analyte-bound particle is accomplished using both physical forces and magnetic forces.

5. The method as defined in claim 3, further comprising introducing into the mixing chamber a plurality of each of: at least one type of conjugate, the at least one type of analyte, and the at least one type of carrier particle; whereby at least one of the analytes binds to a site on at least one of the carrier particles and wherein at least one of the conjugates binds to an other site on the at least one of the carrier particles, thereby forming at least one analyte- and conjugate-bound particle.

6. The method as defined in claim 5 wherein separating includes separating the at least one analyte- and conjugate-bound particle, wherein the other solution includes potential chromophores, and wherein the separated at least one analyte- and conjugate-bound particle reacts with the potential chromophore solution to generate or change a chromophore within the solution, thereby altering the spectrophotometric property of the solution.

7. The method as defined in claim 3 wherein the at least one carrier particle is magnetically responsive, and wherein separating the at least one analyte-bound particle from the fluid by exposing the suspension to magnetic forces is accomplished by generating a magnetic field in the presence of the suspension.

8. The method as defined in claim 3, further comprising transferring the fluidic suspension from the mixing chamber to the optical detection chamber prior to separating.

9. The method as defined in claim 3 wherein the optical detection chamber has physical features defined in or on surfaces thereof.

* * * * *

UNITED STATES PATENT AND TRADEMARK OFFICE
CERTIFICATE OF CORRECTION

PATENT NO.         : 7,384,798 B2
APPLICATION NO. : 11/590263
DATED                : June 10, 2008
INVENTOR(S)       : Philip H. Harding et al.

It is certified that error appears in the above-identified patent and that said Letters Patent is hereby corrected as shown below:

On the Title page, Item (56), under "U.S. PATENT DOCUMENTS", in column 2, line 15, delete "2003/0098302" and insert -- 2003/0096302 --, therefor.

In column 5, line 52, delete "22', 22'" and insert -- 22', 22" --, therefor.

In column 6, line 58, delete "22', 22'" and insert -- 22', 22" --, therefor.

Signed and Sealed this

Eleventh Day of November, 2008

JON W. DUDAS
*Director of the United States Patent and Trademark Office*